United States Patent [19]
Hoyt et al.

[11] Patent Number: 5,304,358
[45] Date of Patent: * Apr. 19, 1994

[54] AIR FRESHENER DEVICE

[75] Inventors: Earl Hoyt, Franklin Lakes, N.J.;
Ralph Muniz, Ste. 3317, 256 S.
Robertson, Beverly Hills, Calif.
90211

[73] Assignee: Ralph Muniz, Beverly Hills, Calif.

[*] Notice: The portion of the term of this patent subsequent to Sep. 22, 2009 has been disclaimed.

[21] Appl. No.: 937,118

[22] Filed: Aug. 31, 1992

[51] Int. Cl.⁵ .............................................. A61L 9/12
[52] U.S. Cl. ...................................... 422/305; 422/4;
422/5; 239/56; 428/13
[58] Field of Search ................. 422/305, 4, 5, 29, 120,
422/122, 123, 306; 239/53, 55, 56, 57, 60, 51.5,
34, 145; 222/187; 261/100-102, DIG. 17;
428/13

[56] References Cited
U.S. PATENT DOCUMENTS

| | | | |
|---|---|---|---|
| 3,807,082 | 4/1974 | Hautmann et al. | 239/55 X |
| 3,964,684 | 6/1976 | Schimanski | 239/57 X |
| 4,197,271 | 4/1980 | Fenstermaker et al. | 422/4 X |
| 4,419,395 | 12/1983 | Sugimoto | 239/56 X |
| 4,484,768 | 11/1984 | Norfleet | 239/56 X |
| 4,549,250 | 10/1985 | Spector | 422/5 X |
| 4,549,693 | 10/1985 | Barlics | 239/55 X |
| 4,714,984 | 12/1987 | Spector | 428/13 X |
| 4,815,659 | 3/1989 | Turko et al. | 239/55 X |
| 5,148,983 | 9/1992 | Muniz | 239/56 |

Primary Examiner—James C. Housel
Assistant Examiner—E. Leigh Dawson
Attorney, Agent, or Firm—Roger Marrs

[57] ABSTRACT

An air freshener device is disclosed herein of multilayer construction which, when laminated or joined together, provides a strong reinforced unitary structure for holding a scented member between two snap-locked layers defining an internally closed cavity that provides a moisture barrier for at least a message or picture card forming a part of the unitary structure. The device includes a pair of thin members having preformed islands, receptacles and pins which, when aligned, may be snap-locked together. A scented member is held in the central cavity defined between the snap-locked members and a plurality of passageways interconnects the central cavity with peripheral vents to release the fragrance exteriorly of the device. Message, photographic or graphic representations are carried on display cards secured to the opposite sides of the snap-locked members which are isolated from the moisture of the scent carried on the scent carrier.

4 Claims, 1 Drawing Sheet

U.S. Patent     Apr. 19, 1994     5,304,358
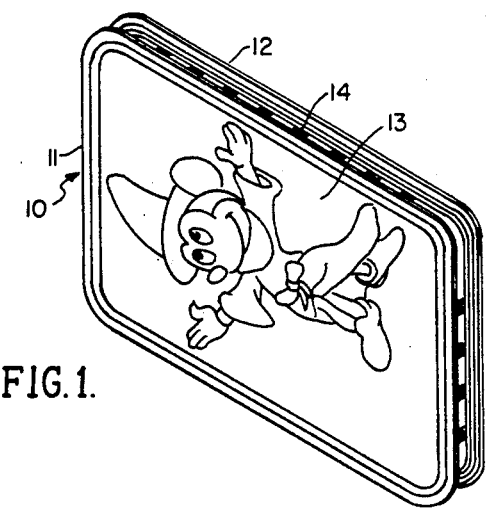
FIG. 1.
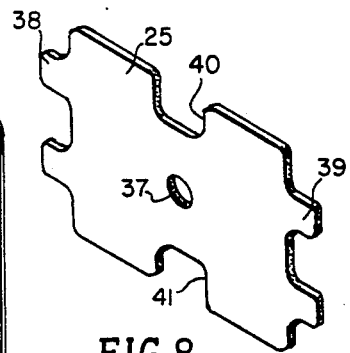
FIG. 8.
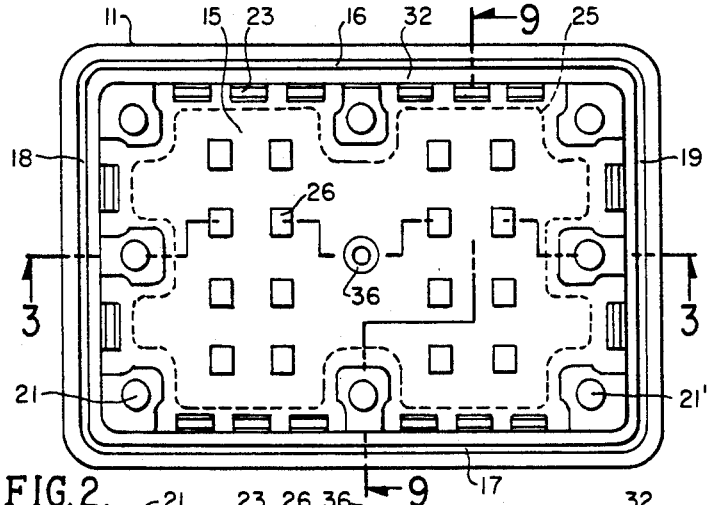
FIG. 2.
FIG. 3.
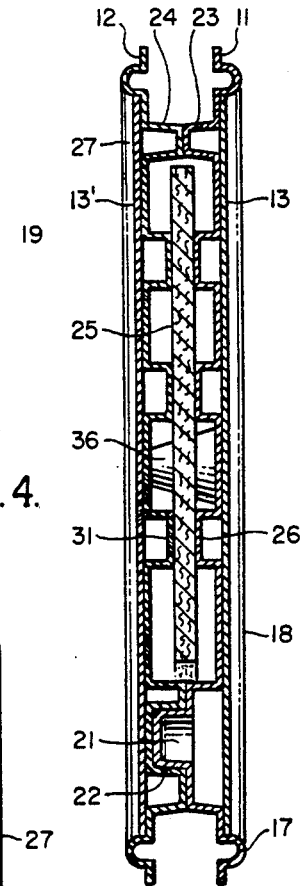
FIG. 4.
FIG. 9.
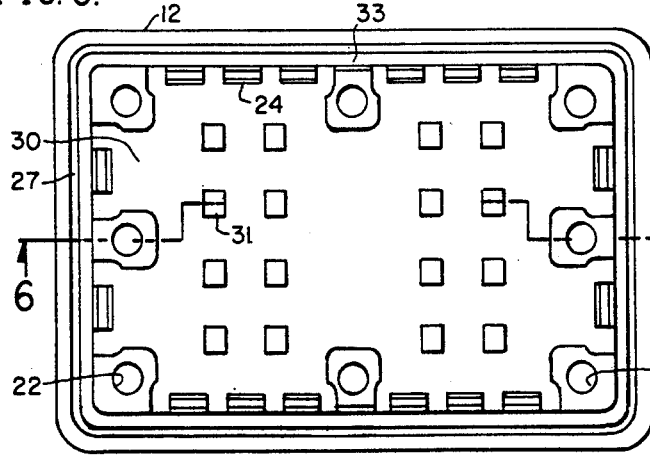
FIG. 5.
FIG. 7.
FIG. 6.

AIR FRESHENER DEVICE

BACKGROUND OF THE INVENTION

1. Field of the Invention

The present invention relates to the field of novelty items, and more particularly to a novel air freshener device having means for holding a scented member in a fixed position within an enclosed cavity so as to prevent moisture from the fragrance or scent from contacting message or pictorial display cards carried on the device, and which further employs multi-layered construction to obtain structural strength and rigidity.

2. Brief Description of the Prior Art

It has been the conventional practice to employ postcards for communicating good cheer, messages, pictorial subject matter or the like from one person to another, utilizing the postal system. However, problems and difficulties have been encountered when using such conventional cards, which stem largely from the fact that the attention characteristics of the card are limited to the visual aspects and do not pertain to other physical senses.

Attempts have been made to augment such cards by employing a variety of means for carrying fragrances or scents so that the released scent will be associated with the subject matter of the card.

Problems and difficulties have been encountered with the conventional approaches, which stem largely from the fact that any fragrance or scent liquid normally absorbs into or onto improperly protected graphic material, especially cardboard or related materials used to communicate the visual message, photograph or graphic representation. Also, the conventional devices employ materials which may be referred to as having a heavy wall, wasteful material and, employment of injection molded structural materials whose function and strength is derived from employment of heavy, resin intensive structural parts. Therefore, such prior devices are heavy and not protective from moisture or other fluids used as the fragrance.

Therefore, a long-standing need has existed to provide a novel air freshener device using a liquid fragrance incorporated into a carrier medium which is isolated from absorbant mediums carrying display indicia. Also, the device should be composed of lightweight materials as individual and separate components which, when combined, provide a reinforced and rigid unitary construction.

SUMMARY OF THE INVENTION

Accordingly, the above problems and difficulties are obviated by the present invention which provides a novel air freshener device having a pair of preformed members with fegisterable islands, receptacles, pins and the like so that when indexed with one another, they provide not only a snap-lock attachment between the member but a hold-down means for retaining a fragrance-carrying member, such as a blotter, between the two members in a cavity. Passageways are incorporated into the preform structure leading to peripheral vents so that the fragrance from the carrier medium will be permitted to discharge exteriorly of the device. The members define the cavity for retaining the fragrance-carrying medium which include a moisture proof retention of the carrier. Display medium is placed on the opposite-sides of the joined members which carry selective indicia, such as designs, messages, graphic representations or the like.

A feature of the invention resides in the fact that each of the individual layers comprising the unitary structure are of thin lightweight material having a high-strength-to-weight ratio and when the components are laminated or joined together, result in a rigid and reinforced structural device.

Therefore, it is among the primary objects of the present invention to provide a novel air freshening device which is composed of multiple layers that are assembled and laminated into a single lightweight configuration which results in high strength and rigidity and which employs materials which are environmentally acceptable.

Another object of the present invention is to provide a novel air freshener comprising component parts of a pre-selected geometry so that selective and efficient use is made of materials having a high strength to weight ratio and which employs extremely simple assembly techniques.

Yet another object of the present invention is to provide a novel air freshener device which includes a thin wall, lightweight structure that contains and dispenses a fragrance in an efficient manner and yet provides a barrier between the graphic display material and the potentially damaging fragrance liquid.

BRIEF DESCRIPTION OF THE DRAWINGS

The features of the present invention which are believed to be novel are set forth with particularity in the appended claims.. The present invention, both as to its organization and manner of operation, together with further objects and advantages thereof, may best be understood with reference to the following description, taken in connection with the accompanying drawings in which:

FIG. 1 is a front perspective view of the novel air freshener device incorporating the present invention;

FIG. 2 is a top elevational view of the first member used in the card shown in FIG. 1;

FIG. 3 is a transverse cross-sectional view of the first member shown in FIG. 2 as taken in the direction of arrows 3—3 thereof;

FIG. 4 is an end elevational view of the first member shown in FIG. 3;

FIG. 5 is a top plan view of the second member used in the device of FIG. 1;

FIG. 6 is a transverse. cross-sectional view of the second member as taken in the direction of arrows 6-6 of FIG. 5;

FIG. 7 is a side elevational view of the second member shown in FIG. 5;

FIG. 8 is a perspective view of the fragrance carrier, such as a blotter or the like, used in the embodiment shown in FIG. 1 as retained in lamination form between the first and second members; and FIG. 9 is a transverse cross-sectional view of the device shown in FIG. 1 wherein the fragrance carrier is sandwiched between the first and second members and with the indicia cards carried on the opposite sides of the device.

DESCRIPTION OF THE PREFERRED EMBODIMENT

Referring now in detail to FIG. 1, the novel air freshener device of the present invention is illustrated in the general direction of arrow 10 which includes a pair of retainer members which are joined together to form an integral, unitary assembly that is rigid, lightweight and reinforced. One member is indicated by numeral 11, while the other member is indicated by numeral 12. Each member includes a recessed cavity defined by a continuous raised sidewall. A display card or the like having a graphic representation, a message or a pictorial representation is mounted in the cavity. The card, including the graphic subject matter, is indicated by numeral 13. It is to be understood that other graphic material may be placed on the retaining member, such as alpha/numeric characters or advertising or other message indicia. Also, it is to be understood that the display area may be on either or both retaining members and that the graphics or indicia pertain to a specified subject matter.

The air freshener device 11 further includes interior passageways having a plurality of peripheral vents, such as vent 14, through which the essence, fragrance or scent of a given characteristic may be communicated exteriorly into the surrounding environment. Preferably, the scent, fragrance or essence conducted exteriorly of the device may be associated with the subject matter or the indicia carried on the display areas on the members 11 and 12. Such dispersal of the scent may augment the association with the graphic or indicia carried on the display area.

Referring now in detail to FIGS. 2 and 3, it can be seen that member 11 is of a rectangular shape or configuration and that an internal cavity, indicated by numeral 15, is defined between raised sidewalls 16 and 17 which are arranged in fixed parallel spaced-apart relationship and are integrally terminated with spaced-apart and parallel end walls 18 and 19. The sidewalls and end walls are continuous and define a recess, indicated by numeral 20 in FIG. 3, and it is to be understood that recess 20 is an exterior recess adapted to receive a display card, such as card 13 shown in FIG. 1. The interior side of the member 11 opposite to the exterior recess 20 includes raised pins, such as pin 21 at the corners which are intended to be snap-locked into receiving receptacles 22, as shown in member 12 in FIG. 5. Also, FIGS. 2–4 inclusive illustrate a plurality of spaced-apart standoffs located about the periphery of the internal cavity 15 in close proximity to the sidewalls and end walls. A typical standoff is indicated by numeral 23 adjacent to wall 16. The standoffs are arranged in spaced-apart relationship so as to provide a means for a fragrance or scent to pass from a fragrance carrier 25, illustrated in broken lines in FIG. 2, and in solid lines in FIG. 8. Also, it is to be noted that the height of the plurality of standoffs is substantially identical to the height of a standoff on which the raised pins 21 are carried. Also, member 11 is provided with a plurality of internally formed projections, such as projection 26, which are used to bear against and support or retain the scented carrier 25 within the internal cavity 15.

Referring now in detail to FIGS. 5, 6 and 7 inclusive, it can be seen that the member 12 includes a similar continuous sidewall and end wall arrangement to the sidewall and end wall arrangement shown in FIG. 2 on member 11. The sidewall in FIGS. 5, 6 and 7 is indicated by numeral 27 and continues about the periphery of the member 12 to define an external cavity, indicated by numeral 28 in FIG. 6. A card similar to the card 13 may be secured within the external cavity 28 so that the subject matter, be it message information or graphic representations, will be readily displayed. Member 12 further includes an internal cavity on the opposite side from the external recess 28 and is indicated in general by the numeral 30 in FIG. 5. The internal cavity is also provided with a plurality of spaced-apart standoffs, such as indicated by numeral 24, which are the same height as the structure defining the recess 22 so that when the members 11 and 12 are snapped together, the pins 21 will fit in registry with the recesses 22 and the respective standoffs 23 on member 11 will register with and bear against the standoffs 24 on member 12. The spaces between adjacent standoffs 24 on card 12 will be indexed with the spaces between adjacent standoffs 23 on card 11 so that vents are defined permitting the essence or fragrance from the saturated blotter carrier 25 to escape through internal passageways leading to the vents. As previously described with respect to member 11, member 12 also includes a plurality of internal projections 31, which are in registry with the projections 26 when the members 11 and 12 are snap-locked together via the raised pins and receptacles.

It is also to be noticed that the external recesses 15 and 30 defined by the end walls and sidewalls include a continuous shoulder, such as shoulder 32 with respect to member 11, and shoulder 33 with respect to member 12, utilized to support the edge marginal region of the card 13 when the respective cards are placed within the external recesses on opposite sides of the device. Numeral 33 pertains to the shoulder, as shown in FIG. 6, and it is in alignment with the linear surface of the member forming the cavities and projections previously described, which are carried on the opposite side of member 12 from the recess 30. In FIG. 3, the shoulder is indicated by numeral 33 and it is in linear alignment with the material of the member forming the projections and raised pins that are exposed on the opposite side of the member from the external recess 20.

FIGS. 2 and 3 further illustrate a central conical guide 36 which is intended to be insertably received through a central opening 37 on the fragrance carrier 25, as shown in FIG. 8. The carrier card 25 further includes a registration means for formfitting the carrier into the internal cavity of member 11 and such means includes laterally extending elements 38 and 39 carried on the opposite ends of the carrier 25 and cutout portions 40 and 41 formed on the sides of the carrier 25. The elements 38, 39 and cutouts 40 and 41 register with the plurality of raised pins along the sides and ends of the respective members and substantially as shown in broken lines in FIG. 2.

FIGS. 1 and 9 illustrate a completely assembled air freshener device with the fragrance carrier, such as a blotter 25, sandwiched between the projections 26 and 31 carried on the respective members 11 and 12. The internal cavities 15 and 16 combine together in the assembly, as shown in FIG. 9, to define an internal cavity occupied solely by the scented carrier 25. The cavity is completely enclosed except for the passageways leading to the vents defined between adjacent projections. The respective cards 13 and 13' as carried on the exterior sides of members 11 and 12 respectively are separated from the internal cavity by the thickness of the respective members so that moist material represented by the fragrance or essence cannot penetrate the material of the card.

In view of the foregoing, it can be seen that a unique, lightweight, thin wall, low cost air freshener device is created which can display graphic material on each of two broad outside surfaces. This inventive concept eliminates the problem of the fragrance liquid wicking into or onto improperly protected graphic material, especially paperboard or related materials used to communicate a visual message or graphic representation. The inventive concept provides a necessary thin wall, lightweight structure to contain and dispense the fragrance efficiently and effectively, yet provide the necessary barrier between the graphic material and the potentially damaging liquid fragrance.

The inventive concept achieves this result via the design of a unique, thin wall, lightweight, five-layer, laminated sandwich panel with an integral center cavity which traps and secures the fragrance carrier, such as blotter 25. The fragrance vent holes around the peripheral edge of the panel are formed by identical projections from each of the two separate members 11 and 12 when the parts are assembled. The individual components of the panel have very little structural strength in the assembled condition and will bend or flex with very little effort. However, when the components are finally assembled into a laminated panel or sandwiched construction, a single lightweight configuration is produced which achieves a strength and rigidity far greater than the sum of the five components. Therefore, a highly efficient, low cost, lightweight, structural device is achieved which has the necessary structural integrity to function well as a consumer product without being wasteful in terms of material usage, such as excessive plastic resin material. Therefore, the inventive concept succeeds in providing a device which is considerate of environmental conditions and it minimizes the use of plastic materials. The inventive concept utilizes a creativity which is in the geometry of the structure itself and this relates to its efficient use of materials, the high strength-to-weight ratio and the extremely simple assembly technique.

While particular embodiments of the present invention have been shown and described, it will be obvious to those skilled in the art that changes and modifications may be made without departing from this invention in its broader aspects and, therefore, the aim in the appended claims is to cover all such changes and modifications as fall within the true spirit and scope of this invention.

What is claimed is:

1. An airfreshener device utilizing high strength-to-weight ratio materials formed into a unitary panel comprising:
   a pair of members composed of high strength-to-weight ratio materials joined together to define an internal storage cavity between their opposing surfaces;
   graphic indicia disposed on at least one exterior face of said joined pair of members;
   each of said members having an exterior continuous peripheral wall defining an exteriorly open recess;
   a display medium carried by at least one of said members in said exteriorly open recess exposing indicia carried on said display medium;
   a pad disposed in said internal storage cavity holding a quantity of a scented substance;
   a wall structure disposed on said pair of members cooperating when joined together to isolate said scented substance from said display medium;
   means internally communicating said scented substance exteriorly of said joined pair of members about the periphery thereof;
   said communicating means comprises a plurality of open-ended passageways extending between said internal storage cavity and edge marginal regions of said joined pair of members;
   said plurality of passageways are defined between opposing surfaces of said members and aligned opposing surfaces of a plurality of raised islands disposed on each of said members;
   said raised islands constitute spaced-apart islands in fixed relationship having top surfaces engageable with the opposing surface of said member opposite to said member carrying said islands;
   said member opposite to said member provided with said islands includes a continuous sidewall defining a cavity insertably receiving said islands and said sidewall having a plurality of vents at the end of each of said passageways for discharging said scented substance;
   raised projections on each of said members extending into said internal storage cavity engaging with opposite sides of said pad to retain said pad therein;
   means integrally disposed on each of said members releasably coupling said pair of members together in a snap-lock relationship;
   said wall structure constitutes a watertight and moisture barrier isolating said scented pad from said display medium.

2. The invention as defined in claim 1 wherein:
   said members, said display means and said pad are individually composed of high strength-to-weight ratio materials constituting layers providing, in combination when joined together, a rigid and non-flexible unitary construction.

3. The invention as defined in claim 2 wherein:
   said pad includes edge cutouts and lateral end extensions cooperating with said islands and projections to act as guides for placement and mounting of said pad within said internal storage cavity.

4. An air freshener device utilizing high strength-to-weight ration materials formed into a unitary panel comprising:
   a pair of members composed of high strength-to-weight ratio materials joined together to define an internal storage cavity between their opposing surfaces;
   graphic indicia disposed on at least one exterior face of said joined pair of members;
   each of said members having an exterior continuous peripheral wall defining an exteriorly open recess;
   a display medium carried by at least one of said members in said exteriorly open recess exposing indicia carried on said display medium;
   a pad disposed in said internal storage cavity holding a quantity of a scented substance;
   a wall structure disposed on said pair of members cooperating when joined together to isolate said scented substance from said display medium; and
   means internally communicating said scented substance exteriorly of said joined pair of members about the periphery thereof;
   said communicating means comprises a plurality of open-ended passageways extending between said internal storage cavity and edge marginal regions of said joined pair of members;
   said wall structure constitutes a watertight and moisture barrier isolating said scented pad from said display medium;

said members, said display means and said pad are individually composed of high strength-to-weight ratio materials constituting layers providing, in combination when joined together, a rigid and non-flexible unitary construction;
said pad includes edge cutouts and lateral end extensions cooperating with said islands and projections to act as guides for placement and mounting of said pad within said internal storage cavity.

* * * * *